United States Patent [19]
Aylsworth et al.

[11] Patent Number: 5,890,490
[45] Date of Patent: Apr. 6, 1999

[54] THERAPEUTIC GAS FLOW MONITORING SYSTEM

[76] Inventors: Alonzo C. Aylsworth, 19359 Ossenfort Ct., Glencoe, Mo. 63038; Gregory R. Miller, #4 Morganfield Ct., Chesterfield, Mo. 63005

[21] Appl. No.: 758,391
[22] Filed: Nov. 29, 1996
[51] Int. Cl.⁶ .......................... A61M 15/00; A61M 16/00
[52] U.S. Cl. .................. 128/203.12; 128/203.25; 128/205.12; 128/205.19; 128/910; 128/911
[58] Field of Search ...................... 128/203.25, 203.12, 128/205.12, 205.19, 910, 911; 73/861.42, 861.44, 861.52

[56] References Cited

U.S. PATENT DOCUMENTS

| | | |
|---|---|---|
| 4,457,303 | 7/1984 | Durkan . |
| 4,462,398 | 7/1984 | Durkan et al. . |
| 4,516,424 | 5/1985 | Rowland . |
| 4,561,287 | 12/1985 | Rowland . |
| 4,627,860 | 12/1986 | Rowland . |
| 4,648,888 | 3/1987 | Rowland . |
| 4,677,975 | 7/1987 | Edgar et al. . |
| 4,681,099 | 7/1987 | Sato et al. . |
| 4,686,975 | 8/1987 | Naimon et al. . |
| 5,134,995 | 8/1992 | Gruenke et al. . |
| 5,137,017 | 8/1992 | Salter . |
| 5,363,842 | 11/1994 | Mishelevich et al. . |
| 5,495,848 | 3/1996 | Aylsworth et al. . |

FOREIGN PATENT DOCUMENTS

| | | |
|---|---|---|
| WO87/04354 | 7/1987 | WIPO . |
| WO90/10470 | 9/1990 | WIPO . |
| WO91/06334 | 5/1991 | WIPO . |

*Primary Examiner*—Mickey Yu
*Assistant Examiner*—Dinh X. Nguyen
*Attorney, Agent, or Firm*—Paul M. Denk

[57] ABSTRACT

A therapeutic gas delivery device includes a monitor having an inlet and an outlet, a source of therapeutic gas in fluid communication with the monitor inlet, and a gas delivery tube in fluid communication with the monitor outlet. The monitor includes a control valve having a normally open port, a normally closed port, and a common port. The common port is connected to the monitor outlet over a gas line and the normally open port and normally closed port are connected to the monitor inlet and atmosphere. The valve is switchable between a first position wherein the therapeutic gas passes through the monitor and a second position wherein atmospheric air or gas passes through the monitor. A flow sensor is placed in the gas line to measure the flow of gas through the second line and produces a signal indicative of the flow of gas through the gas line. A sensor by-pass tube extends around the flow sensor to allow a predetermined portion of the gas to by-pass the flow sensor. A computer is operatively connected to the flow sensor. The computer may be programmed to control the switching of the control valve in response to signals received from the flow sensor.

9 Claims, 7 Drawing Sheets

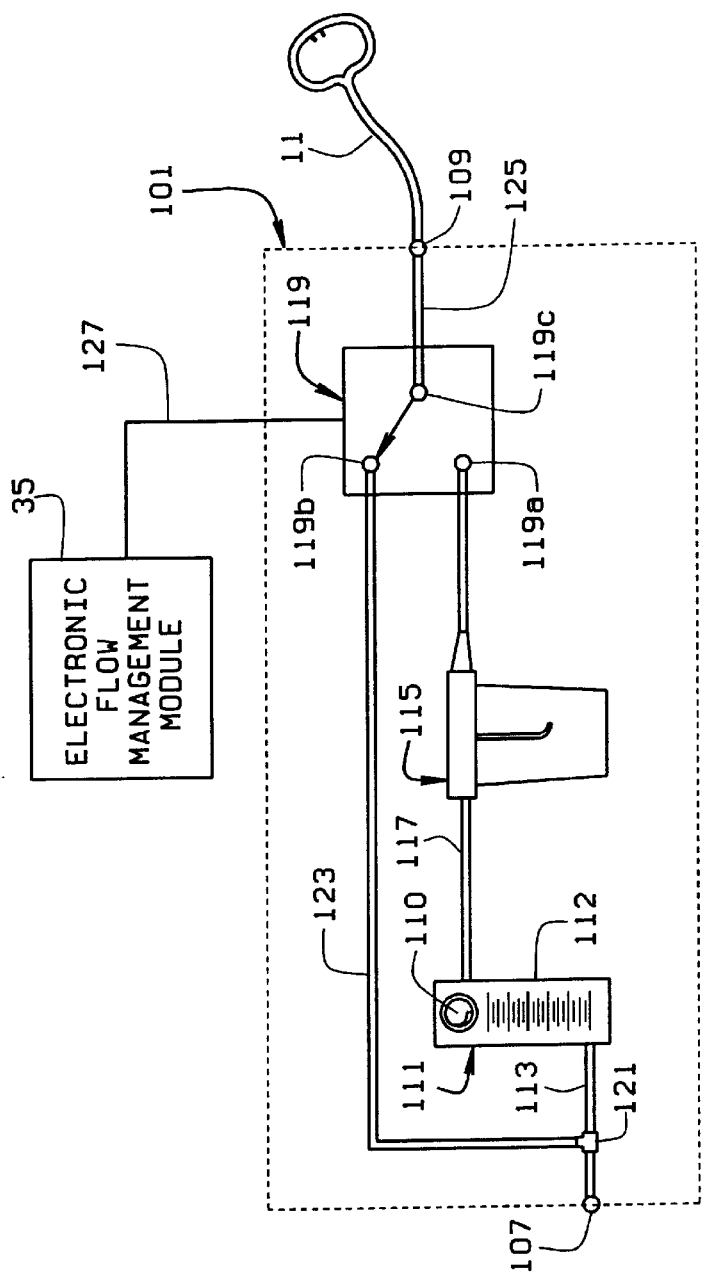
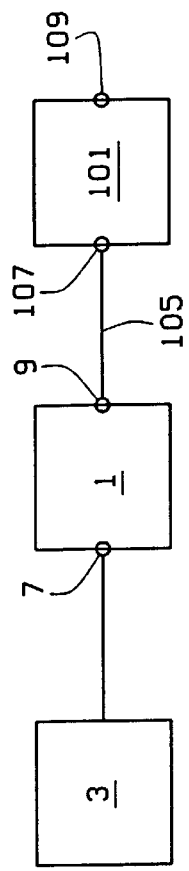
FIG. 4
FIG. 5

THERAPEUTIC GAS FLOW MONITORING SYSTEM

BACKGROUND OF THE INVENTION

This invention relates to an inhalation therapy device, and, in particular to a monitoring device for monitoring and controlling the flow of therapeutic gas.

Generally, a patient with pulmonary disease, breathing disorder or oxygen deficiency is required to breath oxygen provided from a source of oxygen to increase the level, or amount, of oxygen they breath in. The patient is given a prescription that indicates the concentration of oxygen, the flow or volume requirement of oxygen and the use of the oxygen, for example, the hours per day of oxygen delivery. In some cases, the prescription will include the precise hours of the day the patient is to receive the oxygen therapy. For example, the patient's prescription may call for two liters of oxygen per minute for two hours during the day and eight hours at night. Or, in some cases, the prescription may call for four liters of oxygen per minute for twenty-four hours a day. Usually the prescription is based upon oxygen requirements established in a controlled setting, such as during hospitalization. The prescription is continued at home after discharge from the hospital. Delivery of oxygen therapy at home should correspond to the prescription developed in the hospital. Failure to comply with the prescription could be harmful to the patient or less beneficial than planned. Oxygen concentrators have been developed and commercialized to provide the delivery of near pure oxygen to the individual patient to satisfy medical needs. These concentrators can be small and portable. However, once the patient leaves the controlled setting of the hospital, it is difficult to monitor the patient's use of the oxygen to ensure that the is complying with the prescription.

SUMMARY OF THE INVENTION

One object of this invention is to provide a system for monitoring the use of a therapeutic as by a patient to ensure that the patient is receiving appropriate amounts of the gas.

SUMMARY OF THE INVENTION

One object of this invention is to provide a system for monitoring the use of a therapeutic gas by a patient to ensure that the patient is receiving appropriate amounts of the gas.

Another object is to provide such a monitor which can accurately monitor the flow rate of as through the monitor and which can accurately monitor the patient's rate of inhalation.

Another object is to provide such a monitoring system which includes a humidifier to humidify the therapeutic gas.

Another object is to provide such a monitor which delivers the gas in response to patient inhalations.

These and other objects will become apparent to those skilled in the art in light of the following disclosure and accompanying drawings.

In accordance with the invention, briefly stated, a therapeutic gas delivery device is provided. The device includes a monitor having an inlet and an outlet, a source of therapeutic gas in fluid communication with the monitor inlet, and a gas delivery tube in fluid communication with the monitor outlet. The monitor includes a control valve having a normally open port, a normally closed port, and a common port. One of the normally open port and normally closed port is in fluid communication with the monitor inlet over a first line; the common port is in communication with the monitor outlet over a second line, and the other of the normally open port and normally closed port being directed to atmosphere over a third line. The control valve is switchable between a first position wherein the gas from the source of gas passes through the monitor to be breathed in by a patient and a second position wherein atmospheric air or gas passes through the monitor to be breathed in by the patient. A flow sensor is placed in the second line to measure the flow of gas through the second line and produces a signal indicative of the flow of gas through the second line. A sensor by-pass tube extends around the flow sensor to allow a predetermined portion of the gas to by-pass the flow sensor. A restrictor is placed in the by-pass tube to control what the predetermined portion should be. A computer which is operatively connected to the flow sensor to receive the signal from the flow sensor. The computer multiplies the signal from the flow sensor by a predetermined factor to determine the rate of flow of gas through the monitor. The use of the by-pass tube around the flow sensor allows the range of flow rates the sensor can detect to be increased. The computer includes storage means for storing a patient prescription, comparison means, and alarm means. The comparison means compares the signal from the flow sensor to the stored prescription to ensure compliance with the prescription. If the comparison means determines that the prescription is not being complied with, the computer will activate the alarm means. The alarm means may include means, such as an audible or visible alarm, for notifying the patient that the prescription is not being complied with, and/or means, such as a modem, for informing a remote health care provider that the prescription is not being complied with. The computer also stores the data from the sensor. This data may then be downloaded to another computer either directly or over a telephone line. When the control valve is in its first position, the flow sensor detects the rate of flow through the line. When the control valve is in the second position, the sensor can be operated to monitor the patient's breathing rate. Thus, the data storage means stores information relating both to prescription compliance as well as the patient's breathing rate.

The device may be provided with a humidifier positioned between the exit of the by-pass line and the outlet so that the gas exiting the unit will be humidified. A humidifier by-pass line and a second control valve are provided so that the gas will by-pass the humidifier when the unit is operated to monitor a patient's breathing rate. The second control valve has a normally open port, a normally closed port, and a common port. The common port is connected to the monitor outlet and the normally closed and normally open ports are connected to the humidifier and the humidifier by-pass line. Thus, the second control valve can being selectively switched between a first position in which gas inhaled by a patient passes through the humidifier and a second position in which gas inhaled by a patient by-passes the humidifier.

The device may also be provided with a manually controllable flow valve which is selectively settable to control the flow of gas through the monitor. Preferably, the flow valve has a gauge so that the flow of gas through the unit may be visually monitored. The flow valve may be positioned adjacent the humidifier or the inlet of the unit.

The computer means is preferably electronically connected to the control valve to be able to control the switching of the control valve between its first and second positions in response to the signal received from the flow sensor. Preferably, the computer also controls the second control switch so that the humidifier is by-passed when the unit is used to monitor a patient's breathing rate. The unit may be operated to be continuously in a therapeutic gas delivery mode, in which case, the computer does not control the valves. The unit may also be operated so that the computer controls the valve, the computer controls the valves by (a) switching the first control valve to the second position to allow atmospheric gas to pass through the monitor; (b) monitoring the flow of as through the monitor to detect when a user takes a breath; and (c) switching the control valve to the first position to pass therapeutic gas through the monitor for a predetermined amount of time. The computer then cycles through steps (a)–(c) for as long as the monitor is activated. The computer may also initially switch the first control valve to the first monitor is activated. The computer may also initially switch the first control valve to the first position and delivering therapeutic gas for a predetermined amount of time, and then perform and cycle through steps (a)–(c). As noted above, the computer may control the second control valve so that the gas passes through the humidifier at all times, or only when the therapeutic gas is passed through the unit. In any event, the computer will activate the humidifier by-pass when the unit is operated to detect or monitor the patient's breathing rate.

BRIEF DESCRIPTION OF THE FIGURES

FIGS. 3 and 4 are block diagrams of a humidification system connectable to the monitoring system of FIGS. 1 and 2 to humidify the gas with second flow control valves in de-energized and energized states, respectively;

FIG. 5 is a block diagram of the connection of the humidification system connected to the monitoring system of FIG. 1;

DESCRIPTION OF PREFERRED EMBODIMENT

Figure 1:
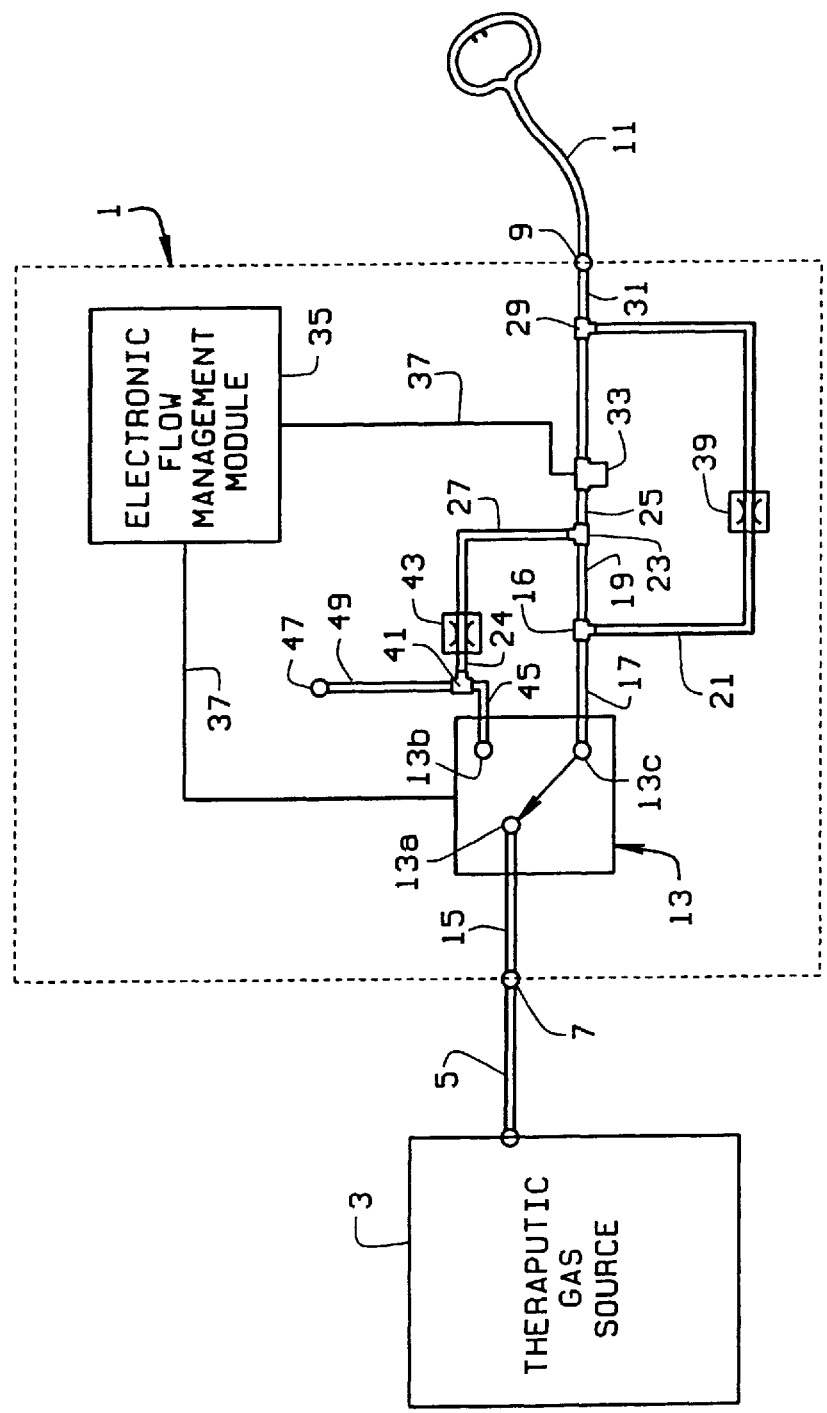
FIG. 1 is a block diagram of one illustrative embodiment of a monitoring system of the present invention with a flow control valve in a de-energized state to deliver therapeutic gas to a patient.

A monitoring system 1 of the present invention is shown generally in FIG. 1. A therapeutic gas source 3 delivers gas (such as oxygen) to the monitor over a tube 5 connected to an input port 7. The therapeutic gas source 3 can be an oxygen generator or oxygen concentrator, liquid oxygen source, high pressure cylinder source, or any other therapeutic gas source, preferably, an oxygen concentrator that provides near pure oxygen. The gas passes through the monitor 1 as will be described below and exits the monitor at an outlet port 9. A nasal cannula 11 is connected to the outlet port 9 and a patient can then breath in the gas which exits the monitor 1. The nasal cannula 11 may also include other patient connected devices, such as an oxygen mask, for example.

The monitor 1 includes a flow control valve 13 having a normally open port 13a, a normally closed port 13b, and a common port 13c. The valve may be a valve such as is commonly available from Humphrey Products, under part no. P6005. The normally open port 13a of valve 13 is connected to the inlet port 7 over a tube 15. The common port 13c of flow control valve 13 is connected to a tee 16 by a tube 17. Tee 16 splits, or divides, the flow of therapeutic gas along two tubes, tubes 19 and 21. Tube 19 is connected to a tee 23 which splits, or divides the flow between tubes 25 and 27. Tube 25 is connected to a third tee 29. The tube 21 feeds into the tee 29 and the tee 29 is connected to the outlet port 9 over a tube 31.

An inhalation sensor/flow sensor 33, such as is manufactured by Microswitch Division of Honeywell of Freeport, Ill., as part no. AWM-3300-V, is inserted in line 25 between tees 23 and 29. The sensor 33 creates signals indicative of the flow through tube 25 (for example in liters/min.). These signals are transmitted to a flow management module 35 over an electrical line 37. The electronic flow management module 35 includes a microprocessor and has data storage capabilities. The microprocessor preferably is a MC68HC05 or better (available from Motorola) and is preprogrammed to operate as will be described below. The management module 33 creates an output signal which travels over an electrical line 37 to control the switching action, or flow control action, of the flow control valve 13 in response to the signal from the sensor 33.

A flow by-pass restrictor 39 is positioned along by-pass tube 21 between tees 15 and 29. The flow by-pass restrictor 39 serves to restrict the flow through tube 21 to a predetermined level. The restrictor 39 may be a valve or a clamp which reduces the diameter of tube 21 to restrict the flow of gas through the tube 21.

Tubing 27 is connected to a fourth tee 41 and an inhalation restrictor 43 is positioned in tube 41 between tees 23 and 41 to restricts or cuts off flow through tubing 27. Tee 41 is connected to the normally closed port 13b of valve 13 over a tube 45 and to an atmospheric port 47 over a tube 49.

Monitoring system 1 functions to detect a patient's breathing patterns and prescription compliance with a respiratory prescription as follows: a patient (not shown) receives oxygen or other therapeutic gas from therapeutic gas source 3 through the nasal cannula 11 according to a physicians prescription. With the flow control valve 13 in the de-energized state, as shown in FIG. 1, the therapeutic gas entering the flow control valve 13 through its normally open port 13a exits the valve 13 through the common port 13c. The gas thus is passed directly from the gas source 3 to the tube 17. The gas will flow through tee 15, tube 19, tee 23, and tube 25 to pass through the inhalation sensor/flow sensor 33. The gas will exit the sensor 33, and pass to the outlet 9 to be inhaled by the patient through the cannula 11. The inhalation sensor/flow sensor 33, in response to the rate of gas inhaled by the patient will create a signal indicative of the gas flow through tube 25. As noted above, this signal will be transmitted to the flow management module 35.

Although all the gas can flow through the tube 25 and sensor 33, preferably a predetermined portion of the flow divided at tee 16 flows through by-pass tube 21 and rejoins the previously divided therapeutic gas at tee 29. By dividing the flow to a predetermined ratio, a more sensitive and precise voltage output is available from inhalation sensor/flow sensor 33. The inhalation sensor/flow sensor 33 preferably used is capable of measuring flow rates from 0 to 1.0 liters per minute. When the flow by-pass restrictor 39 is operated to allow, for example, $5/6^{ths}$ (or 83%), of the gas to flow through the by pass tube 21, only $1/6^{th}$ or 17%) of the gas will pass through tube 25 and sensor 33. Sensor 33 will thus create a signal indicative of $\frac{1}{6}^{th}$ of the actual flow of therapeutic gas to the patient. Thus, in this example, if the sensor 33 detects a flow rate of 0.5 liters per minute the flow management module 35 will multiply the signal by a correction factor of 6 to determine that the patient is receiving 3.0 liters of gas per minute. Other ratios could of course be selected to enable the monitor to detect larger flow rates.

Figure 7:
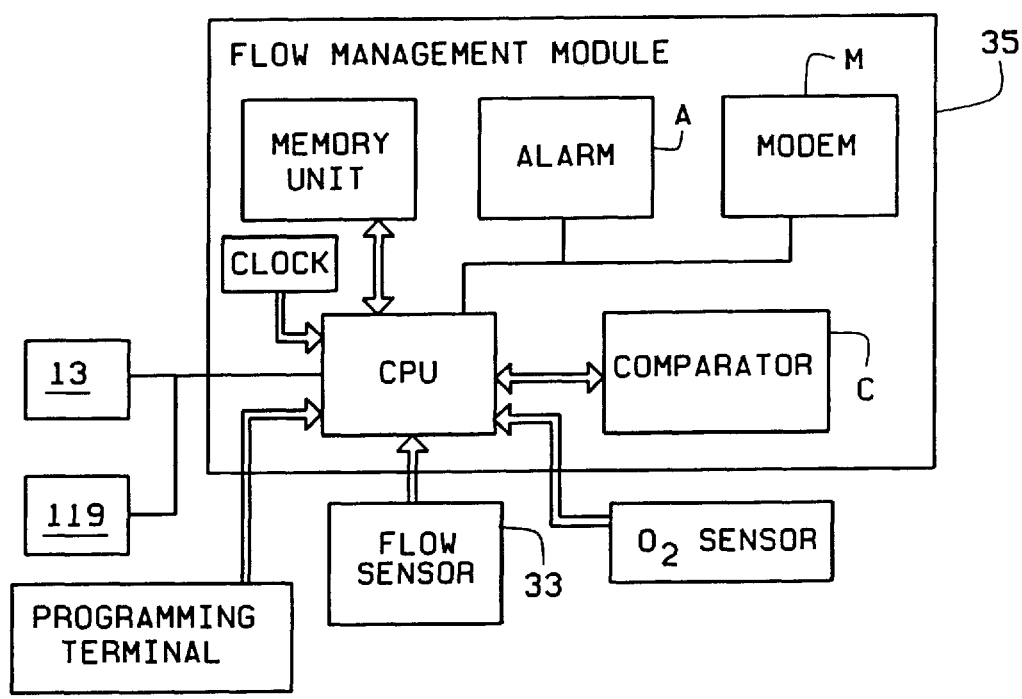
FIG. 7 is a block diagram of a flow management module of the monitor system and its connection to components of the monitor system.

The electronic flow management module 35 is preprogrammed to monitor the flow rate and the time of day of the flow rate to ensure compliance with the patient's prescription, as it is related to flow rate. This information concerning flow rate is electronically stored and may be transmitted to, for example, a personal computer via electronic means such as a modem M (FIG. 7) for review by a physician or other appropriately trained person.

Figure 2:
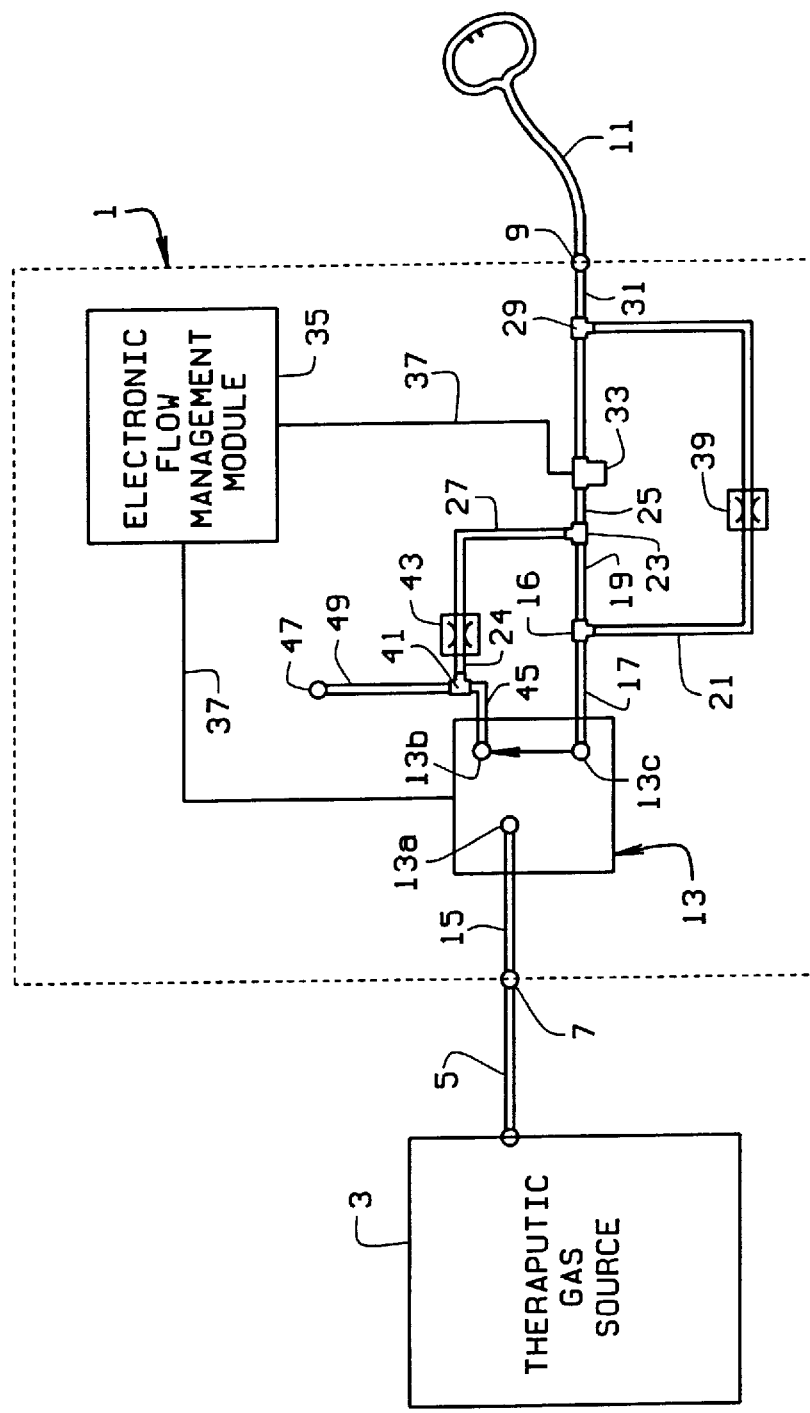
FIG. 2 is a block diagram of the monitoring system with the flow control valve in an energized state to prevent the flow of therapeutic gas to the patient to monitor the patient's breathing rate.

In FIG. 2, the monitor system 1 is shown with the flow control valve 13 in the de-energized state, to place the atmospheric port 47 in fluid communication with the common port 13c of the flow control valve 13. In this state, the flow of the therapeutic gas is interrupted or shut-off at the flow control valve 13 to allow for detection and measurement of a patient's respiratory rate. As a patient breathes, he draws air from the atmosphere through the flow control valve. The air dragon in is passed through the tube 19, the sensor 33, and the by-pass tube 21 as described above. The column of gas drawn through the inhalation sensor/flow sensor 33 as a result of the patient's inhalation is measured as an output voltage from inhalation sensor/flow sensor 33 which is transferred to the flow management module 35. The electronic flow management module 35 thus has the means for determining the presence, rate, and strength of inhalation based upon the flow of ambient air or therapeutic gas across inhalation sensor/flow 33. As previously mentioned, the inhalation sensor/flow sensor 33 is selected to be six times more sensitive than a similar sensor would be to measure normal therapeutic flows of therapeutic gas. As a result, this makes the inhalation sensor/flow sensor 33 much more sensitive to patient inhalations.

As mentioned previously, the importance of prescription compliance is necessary to ensure that the patient receives the full benefit of the delivery of the therapeutic gas prescribed by the physician. The electronic flow management module 35 detects the presence of the patient's breathing and/or rate and strength of inhalations, and logs into memory information such as the time and date of usage or presence of the patient on the nasal cannula 11. Additional information may be logged into memory, for example, respiratory rate, strength of respiratory inhalation along with the date and time that measurements where made. As with flow rate, this information is electronically stored and may be transmitted to, for example, a personal computer via electronic means such as a common modem for review by a physician or other appropriately trained personnel.

As described, when the flow control valve 13 is in its de-energized state (FIG. 1), the inhalation sensor/flow sensor 33 functions to measure the flow rate of a therapeutic gas to a patient and, when the flow control valve 13 is in its energized state (FIG. 2), the inhalation sensor/flow sensor 33 functions as an inhalation sensor to sense presence, rate, and strength of inhalations of the patient. The use of the flow by-pass restrictor 39 allows for use of the sensor 33 to measure both the higher flow rates of therapeutic gas to the patient and to measure the relatively small flow rates of a patient's inhalations.

Although not required for operation of the monitoring system 1, the use of the inhalation restrictor 43 in by-pass tubing 27 cam provide benefit to the patient when flow control valve 13 is de-energized. (FIG. 1) When the valve 13 is de-energized and the inhalation restrictor 43 is opened, a small amount of therapeutic gas will flow from tee 23, through tubing 27, through tee 41, through tubing 49, to exit the monitor 1, through the atmospheric port 47.

It may be desirable in some applications to prevent the entry of atmospheric air into the system 1 beyond tee 23. In such applications, a determination of the length of tubing 49 should be calculated such that the column of therapeutic gas moved through the various tubing of monitor 1 is less than the volume of therapeutic gas in tubing 49. When control valve 13 is energized (FIG. 2), an amount of therapeutic gas fills tubing 49. The patient inhalations will cause the atmospheric air to enter tubing 49, however, the atmospheric air will not enter the monitor 1 past tee 41. The controlled migration of the therapeutic gas into tubing 24 is possible only when flow control valve 13 is de-energized as in FIG. 1. This causes atmospheric air to be flushed from tubing 49. The controlled migration of therapeutic gas into tubing 49 ceases when flow control valve 13 is energized as in FIG. 2 as a result of the discontinued flow of therapeutic gas at flow control valve 13.

Figure 3:
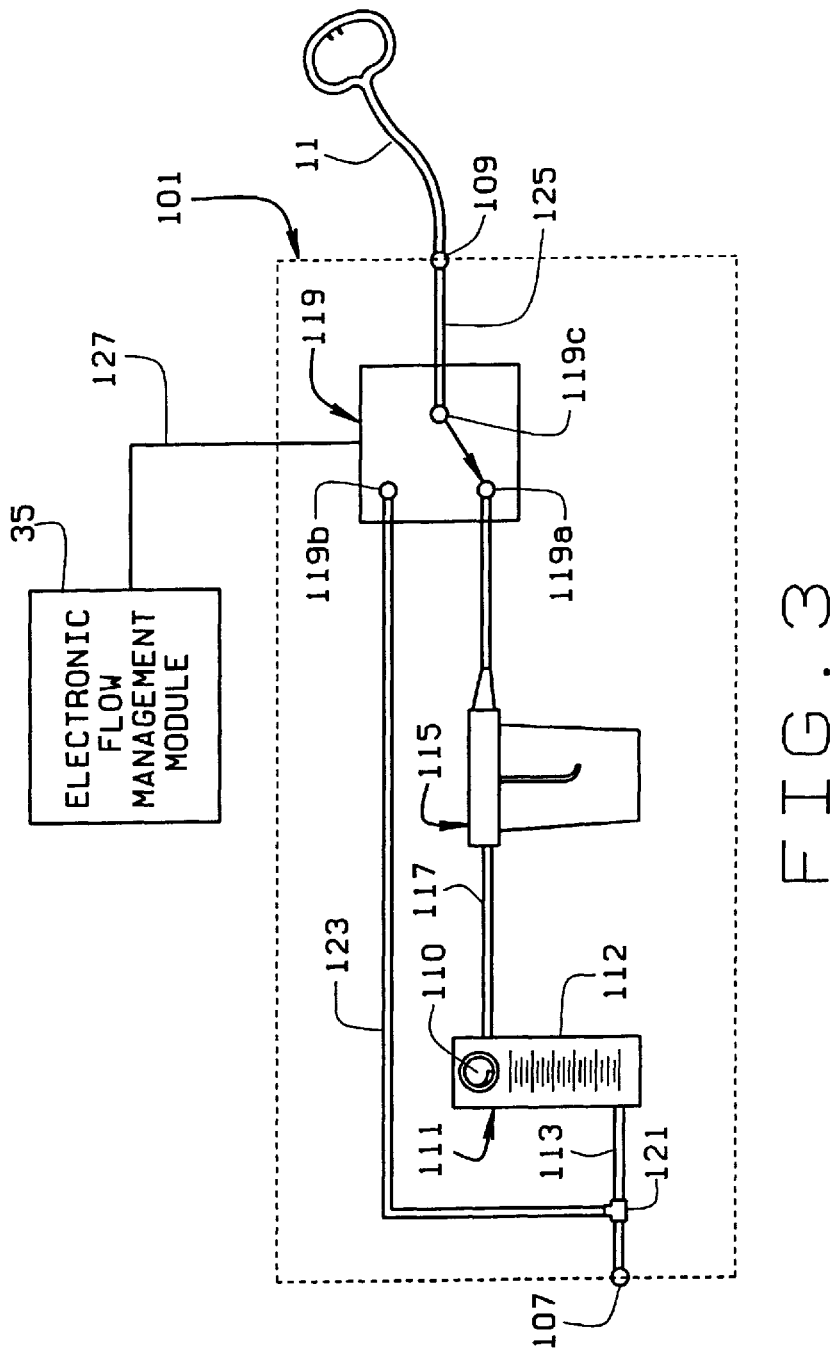

In some applications it is necessary to humidify the therapeutic gas, such as oxygen, and to provide a visual indication of flow of the gas. Without deviating from the scope of this invention, it is possible to employ methods of humidification and flow indications that will not interfere with the ability for the invention to operate as described above. A humidification system 101 which can be connected to the monitoring system 1 is shown in FIGS. 3 and 4. The humidification system 101 has an inlet port 107 and an outlet port 109. The inlet port 107 is connected to the outlet port 9 of system 1 by a tube 105 and the nasal cannula 11 is connected to the outlet port 109. Thus, therapeutic gas passes from the monitoring system 1 to the humidification system 101, and then to the patient through the cannula 11.

The humidification system 101 includes a mechanical flow meter assembly 111, the input of which is connected to the inlet port 107 by a tube 113. The flow meter 111 includes a mechanical flow control 110 Which may be operated to control the amount of gas which flows through meter 111 and a numerical scale or meter 112 which indicates the flow rate through the meter assembly 111. The outlet, of the flow meter assembly 111 is connected to the input of a humidifier bottle 115 by tubing 117. The humidifier bottle 115 is common in the art and could be a humidifier assembly such as part no. 126400 available from Nellcor Puritan-Bennett Corp. of Lenexa, Kans. The outlet of bottle 115 is connected to a normally open port 119a of a flow control valve 119. Valve 119 is preferably similar to the valve 13. A tee 121 is placed in tube 113 between the flow meter assembly 111 and inlet port 107, and a by-pass tube 123 connects the tee 121 to a normally closed port 119b of valve 119. The common port 119c of valve 119 is connected to the outlet port 109 by a tube 125. The valve 119 is controlled by the electronic flow management module 35 of the monitor 1 and is placed in electrical communication therewith by an electrical line 127.

The humidification system 101 functions as follows: When flow control valve 13 is de-energized (FIG. 1), the flow control valve 119 is also de-energized (FIG. 3). This allows the therapeutic gas to flow through the monitoring system 1 as described above. The gas which exits the system 1 enters the humidification system 101 and flows through flow meter assembly 111 and humidifier bottle 115. The gas which enters the humidifier bottle 115 picks up moisture and exits the bottle 115 as humidified gas. The humidified gas then flows through valve 119 and outlet port 109 to be inhaled by a patient via the cannula 11. The use of the meter assembly 111 allows the flow rate of the gas to be adjusted by the mechanical flow control valve 110 and to be monitored by the patient using scale 112.

When flow control valve 119 is energized, as in FIG. 4, therapeutic gas flows into the humidification system 101, but flows through tube 123 to bypass the meter 111 and humidifier bottle 115. Valve 119 is energized when valve 13 is energized. The bypassing of the meter assembly 111 and the bottle 115 allows for maximum sensitivity to the patient's inhalations when the monitoring system is operated to determine a patient's breathing rate.

Figure 6:
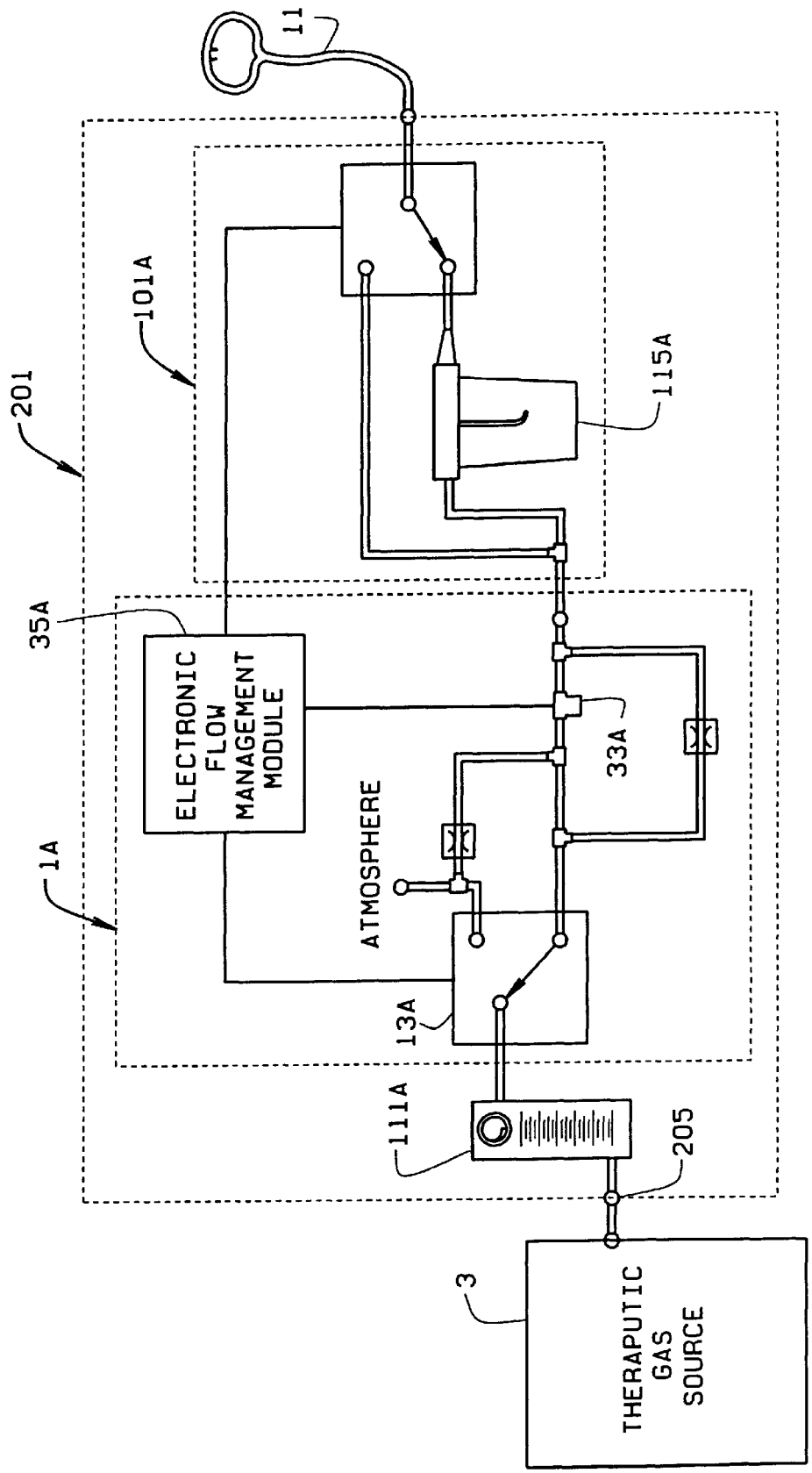
FIG. 6 is a block diagram of a second embodiment of the monitoring system with the flow control valve in a de-energized state.

A second embodiment of the monitor is shown in FIG. 6. The monitor 201 of FIG. 6 incorporates the monitor system 1 and the humidification system 101 into a single unit. As can be seen, the monitoring system 201 includes the monitor portion 1A and the humidification portion 101A. The system differs from that of FIGS. 3–5, however, by installing the flow meter assembly 111A between the inlet 205 and the flow control valve 13A. The flow meter assembly 111A is identical to the flow meter assembly 111.

It is reported that the number one failure of humidified therapeutic gas systems is a leak associated with the humidifier bottle or related pneumatic system components. Such leaks often occur as a result of misapplication by the user, usually after water has been added to humidifier bottle and an inadequate seal is made which results in a leak. In such a case, the electronic flow management module 35A may be preprogrammed with the patient's prescription. This may include flow rate, number of hours the patient should be breathing or creating inhalations of therapeutic gas, the time of day in which therapeutic gas should be delivered and the amount of time therapeutic gas should be delivered. For example, the patient may have ad lusted the flow to 2 liters per minute using the flow meter assembly 111A. If there is a leak in the humidifier bottle 115A or other parts of the pneumatic system, of, for example, 0.5 liter/min., then the inhalation sensor/flow sensor 33A will indicate a therapeutic gas flow rate of 1.5 liters/min. The flow management module includes a comparator means C (FIG. 7) which will compare the flow delivered to the flow prescribed. If the two values are not substantially similar (i.e. within some allowable limit), the flow management module will notify the patient or care giver through electronic means by energizing an appropriate alarm(s) A and/or reporting the event via electronic means, such as a modem M, to alert a remote health care provider or for review by a physician or other appropriately trained person.

Figure 8:
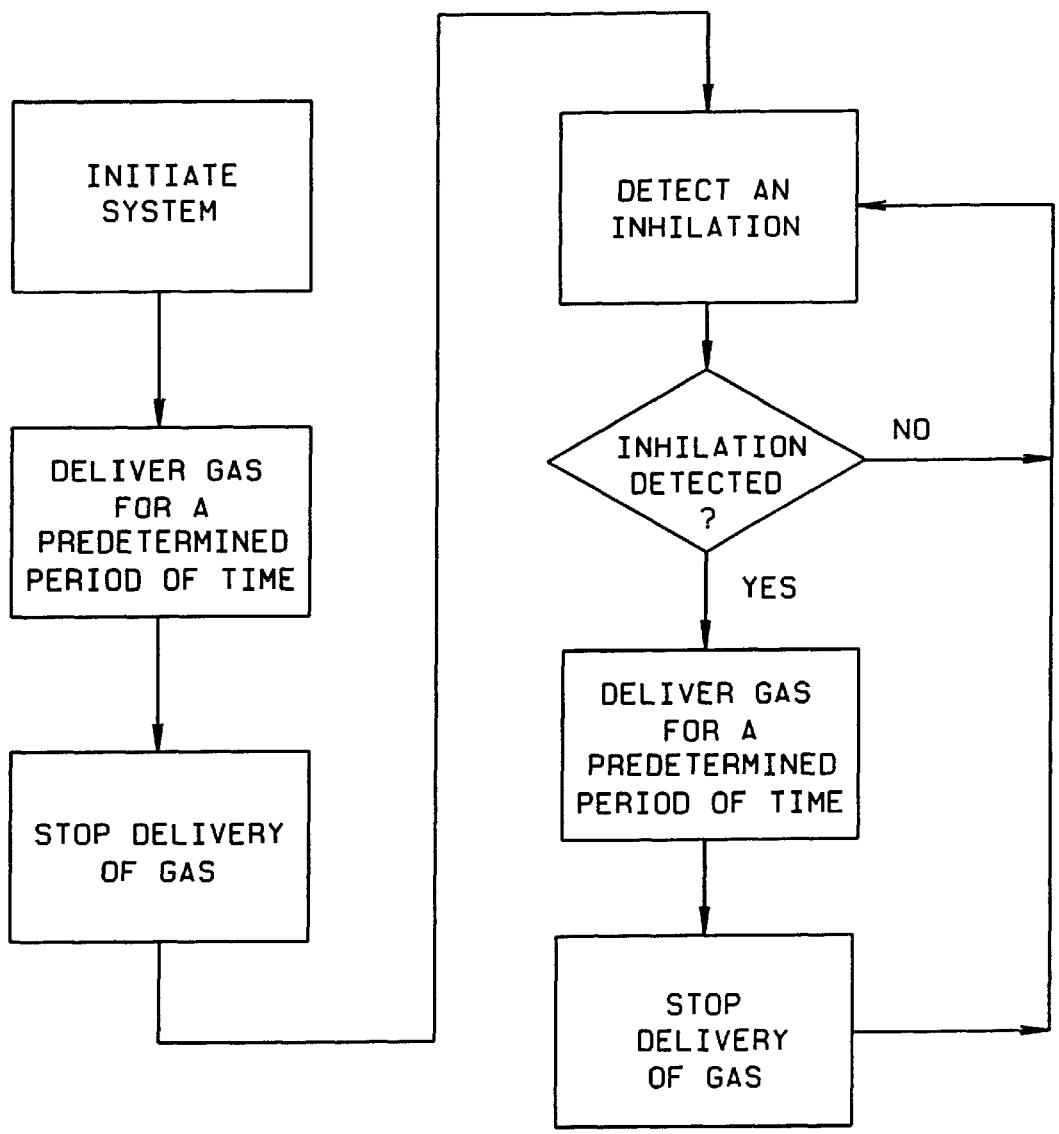
FIG. 8 is a flow chart of the operation of the monitor system in a demand mode.

The monitoring system can also be use in an oxygen conserving or demand device mode. The demand mode is shown diagramatically in FIG. 8. When a demand mode has been selected, a predetermined measure of therapeutic gas is delivered to the patient during a patient inhalation cycle as described below. Turning to FIGS. 1 and 2, the electronic flow module 35 initially energizes the flow control valve 13. When the patient begins breathing through nasal cannula 11, the patient's inhalation is sensed by inhalation sensor/flow sensor 33 which sends a signal along wire 37 to the electronic flow module 35. The electronic flow module 35 processes the inhalation signal and then de-energizes flow control valve 13. The length of time that flow control valve 13 is left in the de-energized state is determined by the programming of the electronic flow module 35, which of course, may be varied to match the most efficient modes of operation that the therapeutic gas source 3 is capable of providing. This will be explained in further detail in this embodiment.

When the monitoring system is operated in a demand mode, it passes between two modes: (1) a delivery cycle and (2) a seek cycle. The system is in a delivery cycle when the flow control valve 13 is de-energized to deliver gas from the source 3 to the patient. The system is in a seek cycle when the flow control valve 13 is energized. Thus, this invention allows predetermined seek and delivery modes to be used to optimize the therapeutic gas source capabilities according to the patient's prescription requirements of the therapeutic gas. For example, it may be desirable, depending upon the therapeutic gas source used by a patient to operate in the delivery mode for the first five minutes of operation. For most oxygen concentrators, this is sufficient time to begin producing therapeutic levels of oxygen for use by the patient. Upon completion of the initial five minute delivery mode, the electronic flow module 35 will energize the flow control valve 13. As the patient breathes through the cannula 11, the inhalation is sensed by inhalation sensor 33, and the sensor 33 determines the flow rate demanded by the patient and sends an appropriate signal o the flow module 35. The flow module 35 then de-energizes the flow control valve 13 for a determined period of inhalations which has been predetermined to be equivalent to continuous delivery of therapeutic gas. For example, the length of time may be 0.5 seconds for delivery mode of operation. After 0.5 seconds of operation in the delivery cycle, the electronic flow module 35 energizes flow control valve 13 and begins the seek cycle. This allows the next patient inhalation to be sensed by inhalation sensor/flow sensor 33. When the next patient inhalation is detected by the electronic flow module 35, the system once again enters into the delivery mode for 0.5 seconds, and then returns to the seek mode.

Programming of the electronic flow module 35 also allows for other operations to be performed. For example, if after a predetermined amount of time, a patient inhalation is not detected, then the electronic control module 35 can de-energize the flow control valve 13 and enter into a continuous delivery mode for a predetermined length of time. Upon completion of predetermined length of time the seek mode may be reinitiated, if necessary, to restart operation of the monitor in the demand mode. Further, it may be desirable during the delivery mode to provide a predetermined number of de-energized/energized states to further conserve therapeutic gas. For example, if the delivery mode time has been predetermined to be 0.5 seconds then it may be desirable to energize and de-energize flow control valve 13 a predetermined number of times during the 0.5 second delivery mode thus pulsing the therapeutic gas being delivered to the patient.

It may also be desirable to incorporate an electronic feedback mechanism including an oxygen sensor which will determine the blood oxygen saturation levels of a patient and deliver a signal indicative of the oxygen saturation levels to the electronic flow management module 35. The oxygen saturation level can be used by the flow management module 35 to control the valve 13 to control the delivery mode time according to the patient's need. A low oxygen saturation level may require a longer delivery time. Such delivery time may also include the length of time oxygen is being pulsed when operating in such a mode. Oxygen saturation measurement devices are available from a number of commercials sources such as Nellcor Puritan Bennett model number N-3000.

Additionally, it may be desirable within the electronic control module 35 to delay the implementation of the demand mode for a predetermined amount of time to, for example, optimize the delivery of therapeutic gas during specific portions of inhalation by the patient. It may also be desirable for example, to delay implementation of demand mode for a predetermined period of time to screen what may appear to the inhalation sensor/flow sensor 33 to be an inhalation when in fact the signal received by the electronic control module 35 from the sensor 33 is movement of the nasal cannula 11. Movement of the cannula 11 may cause a false signal to be detected by inhalation sensor/flow sensor 33. Testing has shown that whipping or movement of the nasal cannula 11 has a different signature upon the onset of the whipping or moving of the nasal cannula 11, than the signal created as result of the onset of the inhalation by the patient. In this mode of operation, the patient benefits as a result of the delivery of therapeutic gas during patient inhalations versus during false sensing which could be created as result of false signals created during, for example, the patient's exercise period when utilizing a treadmill.

Another important feature of this invention is the ability of the electronic control module 35 to monitor the output from the inhalation sensor/flow sensor 33 and to adjust gain or sensitivity of the signal received from the inhalation sensor/flow sensor 33 to maintain sufficient sensitivity to be able to detect the patient's inhalations during varying activities and to measure and monitor the amount of therapeutic gas inhaled by the patient. For example, the strength of the patient's inhalation will vary depending on the patient activity and condition of the patient. The inhalation of the patient will be at one level when asleep and at a different level during exercise. The strength of the inhalation sensed will also vary depending on whether the patient's mouth is open or closed. The electronic control module 35 can adjust the sensitivity level to the patient inhalations to determine the trip point of initiation of delivery mode. The control module can accomplish this by controlling the amount to which restrictor 39 reduces flow through the by-pass tubing 21.

At times, an extension tube may be installed between the outlet port of the monitoring system and the nasal cannula 11. A longer extension tube will allow more patient mobility at the point of use, for example, when moving around in the home when the therapeutic gas source is in a stationary location. When a longer extension tube has been inserted into the outlet port, a reduction in sensitivity is detected by the electronic control module 35 causing corresponding changes in the amount of gain of the signal from sensor 33. This will lead to corresponding changes in the trip point of the initiation of delivery mode of operation. Conversely, when the extension tube is removed and the nasal cannula 11 is connected to the outlet port, a corresponding increase in signal strength, or sensitivity, will cause the gain to be automatically adjusted so that trip point corresponding to inhalation is constant despite the amount of inhalation received by inhalation sensor/flow sensor 33.

As previously mentioned, electronic flow module 35 also has the capability to transmit, via electronic means, the information that would be important for system diagnostics and patient prescription compliance. This information may be transmitted to personal computers or other electronic media, either directly or over a phone line, as may be desired. The electronic flow module 35 also has the capability to receive and transmit electronic data which relates to system diagnostics and patient prescription compliance such as purity levels of oxygen and conservation or demand mode operation. It may also be desirable to eliminate the need for humidification of the oxygen when delivery of oxygen occurs only during patient inhalations (i.e. in a demand mode delivery cycle). This may be desirable to prevent undesired delivery of bacteria that could grow as a result of using external humidification systems.

It is also the intention of this invention to provide the means to externally program the various modes of operation described above. The monitoring system may be operatively connected, for example, by a connection through an RS-232 or an electronic communication port, to a programming terminal. The programming terminal can then be used to preprogram the operation of the monitor to input the prescription into the memory module of the flow management module and to determine:

1.) The therapeutic gas flow rate to be measured.
2.) The adjustments to the flow rate signal that may be necessary because of different densities of the gas.
3.) The monitoring and or detection period of the flow rate.
4.) The sampling rate of flow rate information.
5.) If the patient's use of the gas, as it relates to flow rate and time of day, corresponds to the prescription.
6.) The monitoring and/or detection period of patient inhalations.
7.) The sampling rate of patient inhalation information.
8.) The patient's prescription as it relates to patient inhalation, time of day that patient inhalations should not be detected, and the number of hours that the patient inhalation information is valid within a time period.
9.) The alarm levels of patient flow rate and measured and/or detected patient inhalation rates. The alarm may be stored in memory, made visual and/or audible to patient/user, or may be transmitted via electronic means such as modem to an appropriate care giver.
10.) The ability to enable or disable flow rate and inhalation modes of operation.
11.) The action to be taken upon the detection of a humidifier bottle leak or a related leak in the pneumatic system, i.e. what type of alarm should be activated, for example should the alarm be a visual and/or audible alarms for the patient/user and/or should the alarm be transmitted electronically to an appropriate care giver.
12.) The ability to enter into therapeutic gas conservation methods either independently or in conjunction with previously mentioned modes, including oxygen saturation feedback methods.
13.) The ability to program the conservation mode to optimize the delivery and seek modes by determining the initialization of delivery/seek modes periods delays delivery, seek, the duration of delivery and seek modes, and the logic to reinstate the delivery and seek modes upon an alarm event. An alarm notification means and the sensitivity levels to control the onset of delivery mode and the period of which information pertaining to the operation of the therapeutic gas conservation mode to be logged into memory transmitted via electronic means such as a common modem.
14.) The ability to program the electronic communications means to be used such as modem, radio frequency, including electronic pagers, fiber optics, displays, etc.

It is certainly possible and within the scope of this invention to use the electronic communication port in communication with the electronic control module to provide a 2-way communication for the purpose of prescription historical data from the memory storage located within the electronic flow control management module, to obtain real time data from the monitor, to obtain diagnostic data and prescription instruction as to the set-up of the device.

We have invented a device containing the elements described herein which can measure, monitor and detect flow rate to the patient, log into memory flow rate and time of day to ensure prescription compliance as related to the flow rate, time of flow rate, and time of day. The device also can measure, monitor and detect patient inhalation and patient respiratory rate. The device can be calibrated to provide accurate flow rate information depending upon therapeutic gas, measuring, monitoring, and detecting since different therapeutic gases have different properties. For example, gas density which would affect the accurate operation of the inhalation sensor/flow sensor. The device can measure, monitor, detect the presence, rate, and strength of patients inhalations. The device may log into memory the presence of patient inhalations, respiratory rate, strength respirator, inhalations, and the date and time. The inhalation sensor/flow sensor functions to measure monitor, and detect flows of the therapeutic gas to a patient and because of the use of the predetermined ratio method functions to measure, monitor, detect the presence, rate, and strength of very small flow resulting from the patient inhalations.

The inhalation restrictor method in combination with flow control method flush atmospheric air from the pneumatic system thus preventing contamination of atmospheric air into the therapeutic gas stream.

The humidification by-pass allows for periodic monitoring, measurements, and detection's of patient inhalation respiration rate, and strength of inhalation and still allows for humidification to the therapeutic gas stream. The humidification by-pass method allows for greatly increased sensitivity at the inhlalation sensor/flow sensor when monitoring, measuring, and detecting patient inhalations. Humidifier bottles are restrictive to flow and additionally flow meters are restrictive and could actually interfere with or prevent the ability to monitor, measure and detect the patients inhalations.

The electronic flow management module can be preprogrammed with the patient's prescriptions including but not limited to the flow rate, number of hours the patient should be inhaling the therapeutic gas, time of day, therapeutic gas usage, and amount of time the therapeutic gas should be delivered. This information is stored in memory and can be used to notify through electronic means or alarm methods both the patient/user or other appropriately trained personnel as to the patients compliance to the prescription. The device can be used for the detection of humidifier bottle leaks in the pneumatic system and can notify through the electronics means or alarm methods both the patient/user or other appropriately trained personnel as to the patients compliance to the prescription. This information can also be stored into memory. The device can be preprogrammed for therapeutic gas conservation mode whereas a predetermined measure of therapeutic gas is delivered to the patient in response to the patient inhalations. Optimization of delivery and seek modes can be preprogrammed through electronic means and stored in memory. Optimization parameters include but is not limited to:

the initialization of delivery mode
the initialization of seek mode
the oxygen saturation feedback mode
any delays of delivery and/or seek modes
duration of delivery and/or seek modes
the alarm means to enter into continuous delivery of therapeutic gas
the means to reinitiate delivery and/or seek modes after entering an alarm mode.
the ability to monitor, log, and report the functioning and detection of the therapeutic conservation mode and to store such information in memory.

The device includes electronic means to screen out false signals that could be interpreted as patient inhalations.

The device provides for sensitivity adjustment means to monitor inhalation sensor/flow sensor outputs and adjust sensitivity levels to control the onset of delivery of therapeutic gas. During therapeutic gas conservation mode sensitivity is adjusted to accommodate patient condition, activity, or delivery method of therapeutic gas.

This device includes electric means to preprogram the operation of the device by communication means such as a modem, radio frequency transmission and reception techniques (including pagers), fiber optic techniques, etc.

This device includes a microprocessor and associated memory storage and date/time circuitry.

We claim:

1. A therapeutic gas delivery device including a monitor having an inlet and an outlet, a source of therapeutic gas in fluid communication with the monitor inlet, and a gas delivery tube in fluid communication with the monitor outlet; the monitor including a control valve having a normally open port, a normally closed port, and a common port; one of the normally open port and normally closed port being in fluid communication with the monitor inlet over a first line; the common port being in communication with the monitor outlet over a second line; the other of the normally open port and normally closed port being directed to atmosphere over a third line; the control valve being switchable between a first position wherein the gas from the source of gas passes through the monitor to be breathed in by a patient and a second position wherein atmospheric air passes through the monitor to be breathed in by the patient;

a flow sensor in the second line to measure the flow of gas through the second line, the sensor producing a signal indicative of the flow of gas through the second line;

a by-pass line for by-passing a predetermined portion of the gas around the sensor, the by-pass line having an inlet upstream from the sensor and an exit down stream from the sensor;

a restrictor in the by-pass line for setting the amount of gas which will pass through the by-pass line and the amount of gas which will pass through flow sensor;

a computer means which is operatively connected to the flow sensor to receive the signal from the flow sensor, the computer means including multiplication means for multiplying the signal from the flow sensor by a predetermined factor to determine the rate of flow of gas through the monitor;

said computer means including storage means for storing a patient's prescription, comparison means, and alarm means;

the computer means includes data storage means for storing the predetermined flow rates of gas through the monitor and means for transferring the stored flow rate data to a remote health care provider, said data storage means includes means for storing flow rates of therapeutic gas through the monitor and flow rates of atmospheric air through the monitor;

a third line is connected to the second line over a fourth line, the fourth line intersecting the second line upstream of the flow monitor, a second restrictor being placed in the fourth line to control the amount of atmospheric air passing through the monitor; and the comparison means comparing the signal from the flow sensor to the stored prescription to ensure compliance with the prescription, the computer means activating the alarm means if the prescription is not being complied with.

2. The device of claim 1 wherein the alarm means includes means for notifying the patient that the prescription is not being complied with, means for informing a remote health care provider that the prescription is not being complied with, or combinations thereof.

3. The device of claim 1 wherein the computer means is electronically connected to the control valve switch the control valve between its first and second positions in response to the signal received from the flow sensor.

4. The device of claim 1 including a humidifier positioned between the exit of the by-pass line and the outlet, the gas passing through the humidifier to be humidified.

5. The device of claim 4 including a humidifier by-pass line and a second control valve, the second control valve having a normally open port, a normally closed port, and a common port; the common port being connected to the monitor outlet, one of the normally open port and the normally closed port being in communication with the humidifier, and the other of the normally open port and normally closed port being in communication with the humidifier by-pass line; the second control valve being selectively switchable between a first position in which gas inhaled by a patient passes through the humidifier and a second position in which gas inhaled by a patient by-passes the humidifier.

6. The device of claim 5 wherein the computer means is electronically connected to both the first control valve and the second control valve to control the position of both said valves.

7. The device of claim 4 including a manually controllable flow valve which is selectively settable to control the flow of gas through the monitor, the flow valve including a gauge to monitor the flow of gas through the monitor.

8. The device of claim 7 wherein the flow valve is positioned adjacent the humidifier.

9. The device of claim 7 wherein the flow valve is positioned at the inlet of the monitor unit.

\* \* \* \* \*

UNITED STATES PATENT AND TRADEMARK OFFICE
CERTIFICATE OF CORRECTION

PATENT NO.   : 5,890,490
DATED        : April 6, 1999
INVENTOR(S)  : Aylsworth, Alonzo C., et al.

It is certified that error appears in the above-indentified patent and that said Letters Patent is hereby corrected as shown below:

Column 13, claim 3, line 15, after "control valve" insert ---to---

Signed and Sealed this

Twenty-eighth Day of September, 1999

Q. TODD DICKINSON

*Attest:*

*Attesting Officer*           *Acting Commissioner of Patents and Trademarks*